United States Patent
Cao et al.

(10) Patent No.: US 12,421,494 B2
(45) Date of Patent: *Sep. 23, 2025

(54) METHOD FOR EX-VIVO EXPANSION OF REGULATORY T CELLS WITH ENHANCED SUPPRESSIVE FUNCTION FOR CLINICAL APPLICATION IN IMMUNE MEDIATED DISEASES

(71) Applicant: Therakos Development Limited, Dublin (IE)

(72) Inventors: Tinghua Cao, Malvern, PA (US); Li Li, Downington, PA (US)

(73) Assignee: Therakos Development Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/584,070

(22) Filed: Feb. 22, 2024

(65) Prior Publication Data

US 2024/0191193 A1    Jun. 13, 2024

Related U.S. Application Data

(60) Continuation of application No. 17/515,985, filed on Nov. 1, 2021, now abandoned, which is a division of application No. 15/981,332, filed on May 16, 2018, now Pat. No. 11,186,823, which is a continuation of application No. 15/094,467, filed on Apr. 8, 2016, now abandoned, which is a continuation of application No. 12/781,451, filed on May 17, 2010, now abandoned.

(60) Provisional application No. 61/179,165, filed on May 18, 2009.

(51) Int. Cl.
| | | |
|---|---|---|
| C12N 5/0783 | (2010.01) | |
| A61K 35/12 | (2015.01) | |
| A61K 40/11 | (2025.01) | |
| A61K 40/22 | (2025.01) | |
| A61K 40/41 | (2025.01) | |

(52) U.S. Cl.
CPC ............ *C12N 5/0637* (2013.01); *A61K 40/11* (2025.01); *A61K 40/22* (2025.01); *A61K 40/416* (2025.01); *C12N 5/0636* (2013.01); *A61K 2035/122* (2013.01); *C12N 2501/23* (2013.01); *C12N 2501/2302* (2013.01); *C12N 2501/51* (2013.01); *C12N 2501/515* (2013.01)

(58) Field of Classification Search
CPC .......... A61K 39/4621; A61K 39/46433; A61K 39/4611; A61K 35/122; C12N 5/0636; C12N 5/0637; C12N 2501/2302; C12N 2501/51; C12N 2501/515
See application file for complete search history.

(56) References Cited

U.S. PATENT DOCUMENTS

| | | |
|---|---|---|
| 2003/0049696 A1 | 3/2003 | Norment et al. |
| 2005/0186207 A1 | 8/2005 | Bluestone et al. |
| 2007/0009497 A1 | 1/2007 | Steinman et al. |
| 2008/0175830 A1 | 7/2008 | Steinman et al. |
| 2017/0096636 A1 | 4/2017 | McIver et al. |

FOREIGN PATENT DOCUMENTS

| | | |
|---|---|---|
| JP | 2004527263 A | 9/2004 |
| JP | 2007538000 A | 12/2007 |
| JP | 2011504202 A | 2/2011 |
| JP | 2012525403 A | 10/2012 |
| WO | 2009024348 A1 | 2/2009 |

OTHER PUBLICATIONS

Cao T., et al . . . , "Ex Vivo Expanded Human CD3+CD25+Foxp3+ Regulatory T Cells Prevent Lethal Xenogenic Graft Versus Host Disease (GVHD)," Cellular Immunology, Academic Press, San Diego, CA, Jan. 1, 2009, vol. 258 (1), pp. 65-71.
Communication Pursuant to Article 94(3) EPC for European Application No. 10778215.3, dated Aug. 9, 2016, 5 pages.
Decision to refuse a European patent application (Art. 97(2) EPC) for European Application No. 10778215.3, dated Nov. 17, 2017, 06 pages.
Earle K.E., et al., "In Vitro Expanded Human CD4+CD25+ Regulatory T Cells Suppress Effector T Cell Proliferation," Clinical Immunology, 2005, vol. 115, pp. 3-9.
Larche, Chest, 2007, vol. 132 (3), pp. 1007-1014.
Longhi, Maria Serena et al., "Expansion and De Novo Generation of Potentially Therapeutic Regulatory T Cells in Patents with Autoimmune Hepatitis," Hepatology, Feb. 7, 2008, vol. 47 (2), pp. 581-591.
Notification of Reasons for Refusal (Office Action), Corresponding JP Application No. 2012511969, Japanese Patent Office, Aug. 26, 2014), 5 pages.
Office Action for U.S. Appl. No. 17/515,985, mailed on Apr. 26, 2023, 22 pages.
Putnam, Amy L., et al., "Expansion of Human Regulatory T Cells From Patents With Type 1 Diabetes, " Diabetes, American Diabetes Association, vol. 58 (3) , Mar. 1, 2009, pp. 652-662.
Scalping, Kenneth et al., "Suppression of Disease in New Zealand Black/New Zealand White Lupus-Prone Mice by Adoptive Transfer of Ex Vivo Expanded Regulatory T Cells," The Journal of Immunology, Aug. 1, 2006, vol. 177 (3), pp. 1451-1459.
Sumida, Y. et al., Journal of Gastroenterology, Japanese Society of Gastroenterology, 2008, vol. 105 (Extra Edition), p. A200.
Sumida, Y., et al., "Preparation of Functionally Preserved CD4+ CD25high Regulatory T Cells From Leukapheresis Poroducts From Ulcerative Colitis Patients, Applicable to Regulatory T-Cell Transfer Therapy," Cytotherapy, International Society for Cellular Therapy, Vancouver, Canada, 2008, vol. 10 (7), pp. 698-710.

(Continued)

Primary Examiner — Robert A Zeman
(74) Attorney, Agent, or Firm — POLSINELLI PC

(57) ABSTRACT

The invention provides methods for the ex-vivo expansion of CD4+CD25+ Tregs. The invention provides a method for producing ex vivo expanded Tregs that may be used to inhibit unwanted human immune responses against self-antigens or allergens. Additionally, the ex vivo expanded Tregs may provide treatment for inflammatory/autoimmune diseases.

12 Claims, 5 Drawing Sheets

(56) References Cited

OTHER PUBLICATIONS

Summons to Attend Oral Proceedings Pursuant to Rule 115(1) EPC for European Application No. 10778215.3, dated May 2, 2017, 09 pages.
Supplementary European Search Report, Corresponding European Application No. 10778215, European Patent Office, May 15, 2013, 9 pages.
Tang Q., et al., "In Vitro-Expanded Antigen-Specific Regulatory T Cells Suppress Autoimmune Diabetes," Journal of Experimental Medicine, 2004, vol. 199, pp. 1455-1465.
Tarbell K.V., et al., "CD25+ CD4+ T Cells, Expanded with Dendritic Cells Presenting a Single Autoantigenic Peptide, Suppress Autoimmune Diabetes," Journal of Experimental Medicine, New York, Jun. 7, 2004, vol. 199 (11), pp. 1467-1477.
Yamakazi, et al., "Effective Expansion of Alloantigen-Specific Foxp3+CF25+CD4+ Regulatory T Cells by Dendritic Cells During the Mixed Leukocyte Reaction," Proceedings of the National Academy of Sciences of the United States of America (PNAS), 2006, vol. 103, pp. 2758-2763.

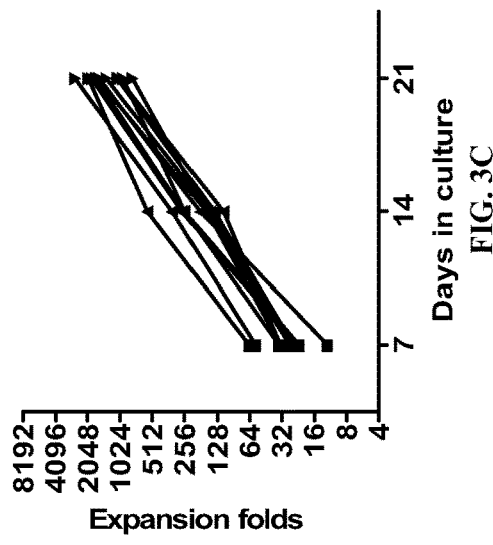
FIG. 3A SLE
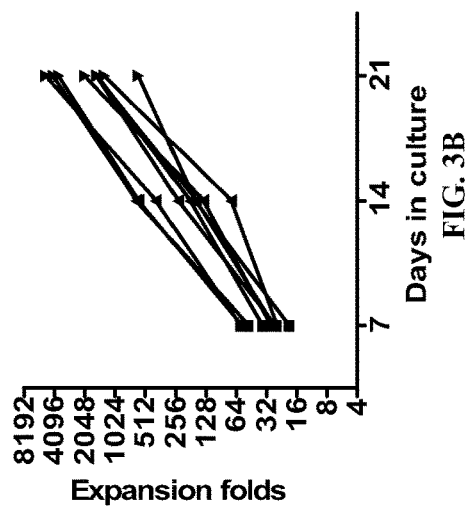
FIG. 3B Asthma
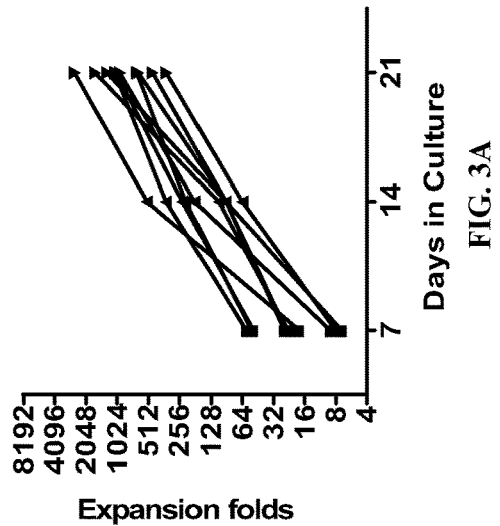
FIG. 3C RA
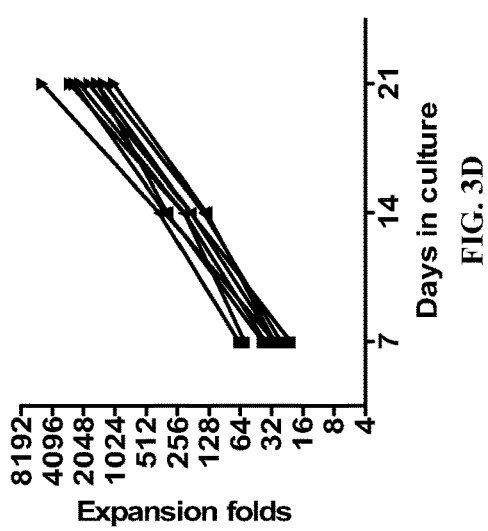
FIG. 3D MS
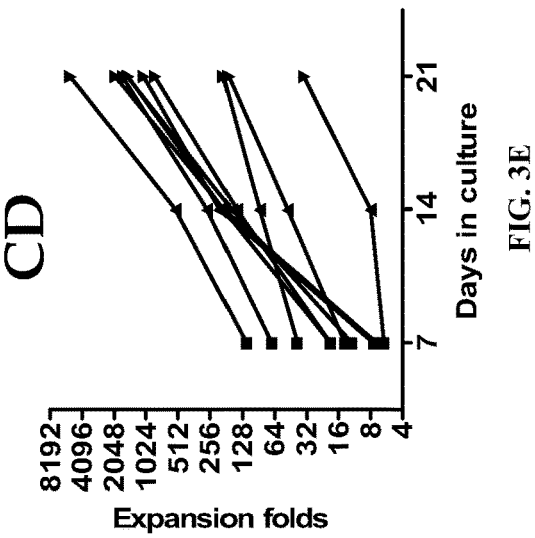
FIG. 3E CD
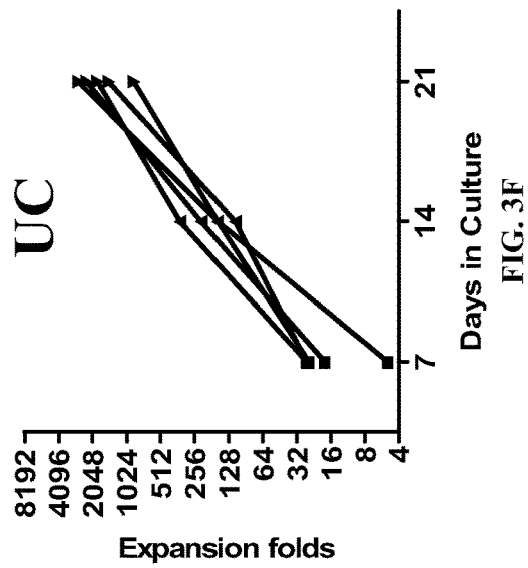
FIG. 3F UC

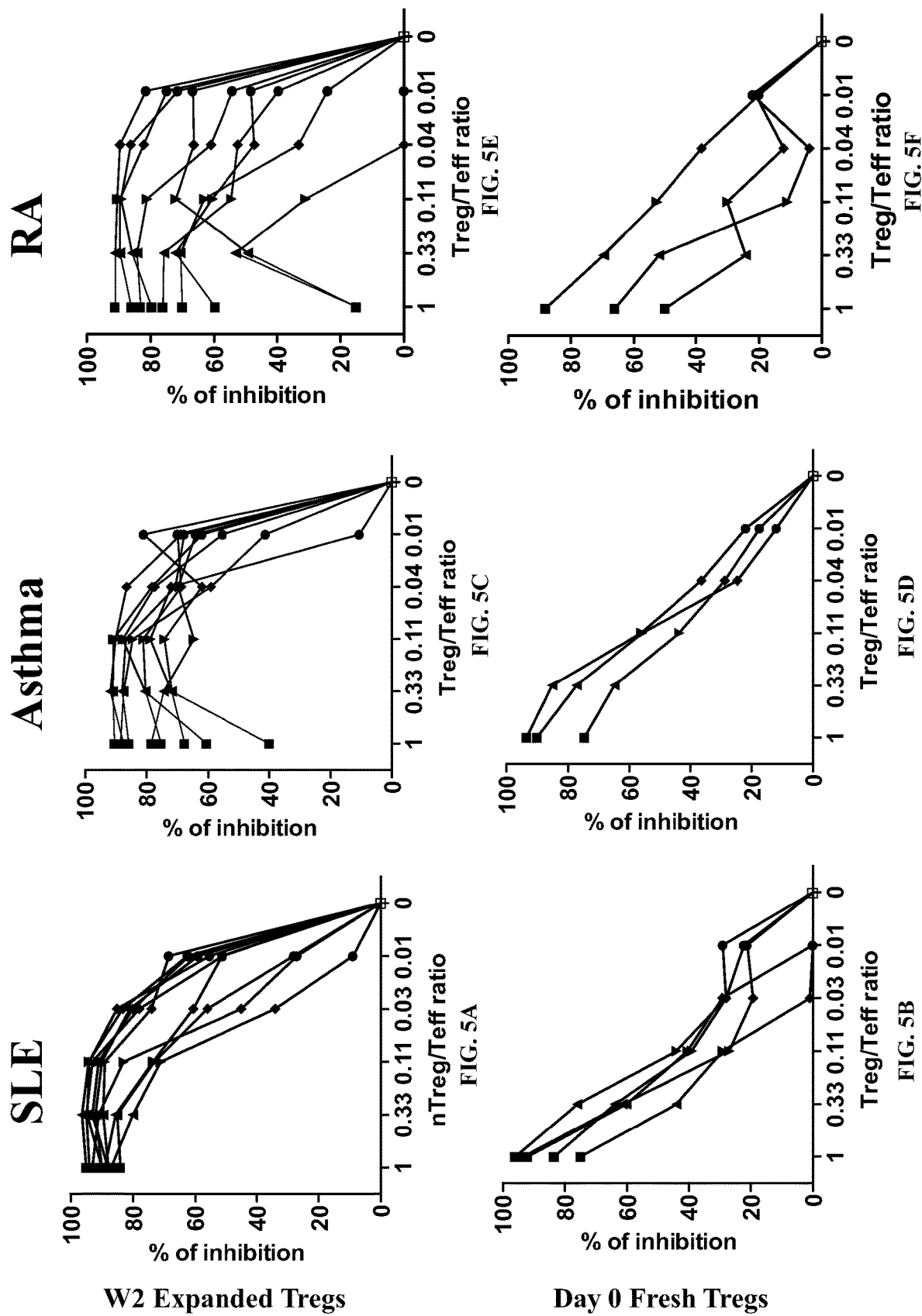

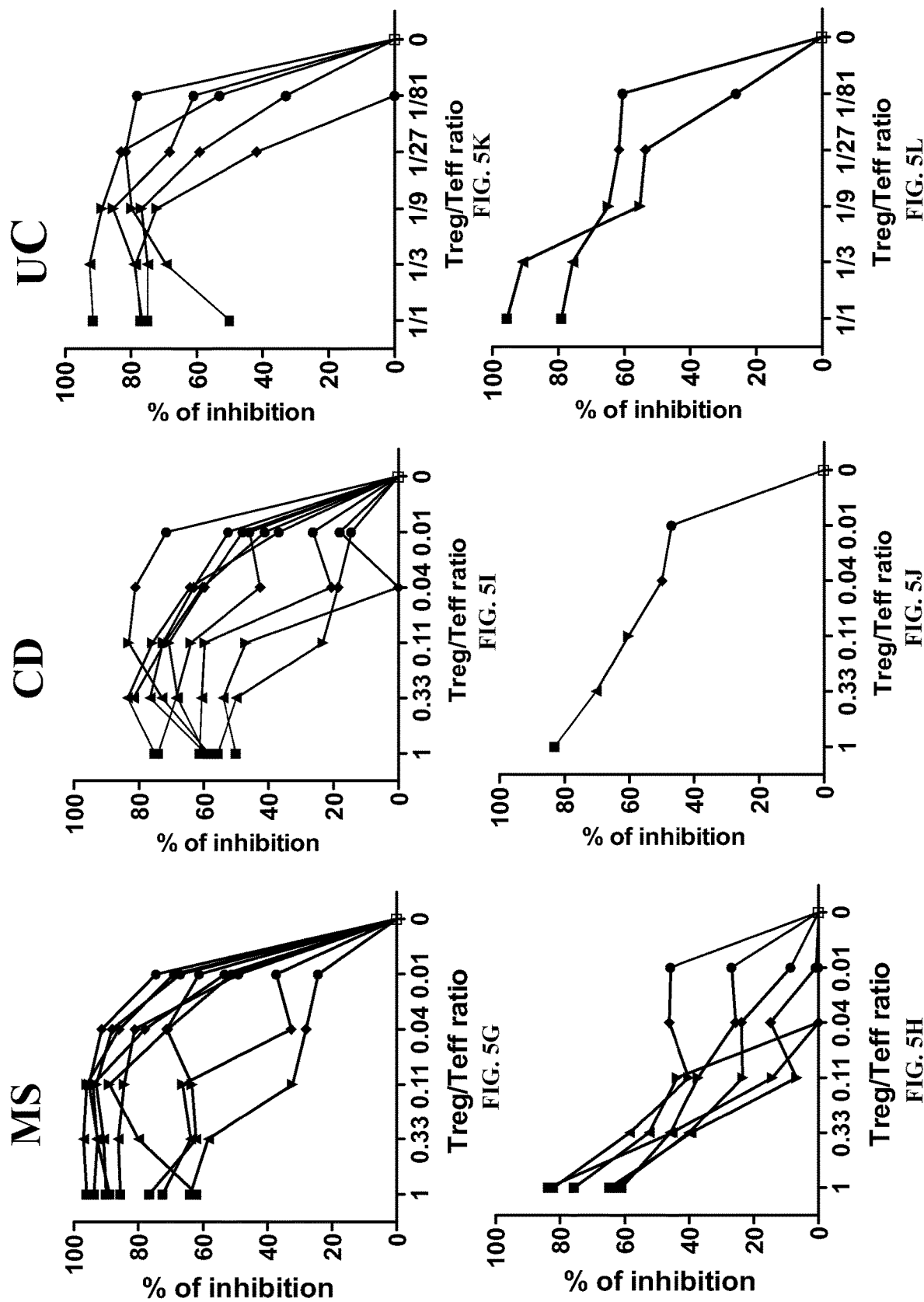

METHOD FOR EX-VIVO EXPANSION OF REGULATORY T CELLS WITH ENHANCED SUPPRESSIVE FUNCTION FOR CLINICAL APPLICATION IN IMMUNE MEDIATED DISEASES

CROSS REFERENCE TO RELATED APPLICATIONS

This application is a continuation of U.S. patent application Ser. No. 17/515,985, filed on Nov. 1, 2021 (now abandoned) which is a divisional of U.S. patent application Ser. No. 15/981,332, filed on May 16, 2018 (now U.S. Pat. No. 11,186,823) which is a continuation of U.S. patent application Ser. No. 15/094,467, filed on Apr. 8, 2016 (now abandoned), which is a continuation of U.S. patent application Ser. No. 12/781,451, filed on May 17, 2010 (now abandoned), which claims the benefit of U.S. Provisional Application No. 61/179,165, filed May 18, 2009. The entire disclosure of each application that is set forth in this Cross Reference to Related Applications section is hereby incorporated by reference.

FIELD OF THE INVENTION

The invention relates to methods for enhancing the suppressive function of regulatory T cells. In particular, the invention provides a method for ex-vivo expansion of regulatory T cells, which cells demonstrate enhanced suppressive characteristics.

BACKGROUND OF THE INVENTION

Regulatory T cells, or Tregs, are known to be critical in maintaining a tolerance to self-antigens by suppressing the activation of the immune system. In person with inflammatory/autoimmune diseases, such as systemic lupus erythematous, multiple sclerosis, rheumatoid arthritis, asthma, ulcerative colitis, and Crohn's Disease, there is a functional defect or frequency decrease in the transcription factor Foxp3 expressing CD4+CD25+Tregs. In such autoimmune diseases, the person's immune system fails to recognize cells, or parts of cells as the person's own resulting in tissue destruction.

The therapeutic effects of administration of CD4+CD25+ Tregs has been shown in the treatment of a variety of animal disease models including, without limitation, rheumatoid arthritis, asthma, and graft-versus-host disease ("GVHD"). Use of Tregs in treatment applications is problematic because they are present as only a very small percentage, approximately 1 to 2%, of human peripheral blood mononuclear cells. Thus, methods of activating and expanding, or proliferating, Tregs ex-vivo have been developed for use in the treatment of certain diseases.

BRIEF DESCRIPTION OF THE DRAWINGS

FIGS. 3A-3F are a graphs showing the Treg expansion of Example 3.

FIGS. 5A-5L are a graphs showing the inhibitory activity of the expanded Tregs of Example 4.

DETAILED DESCRIPTION OF THE INVENTION AND PREFERRED EMBODIMENTS

Figure 1:
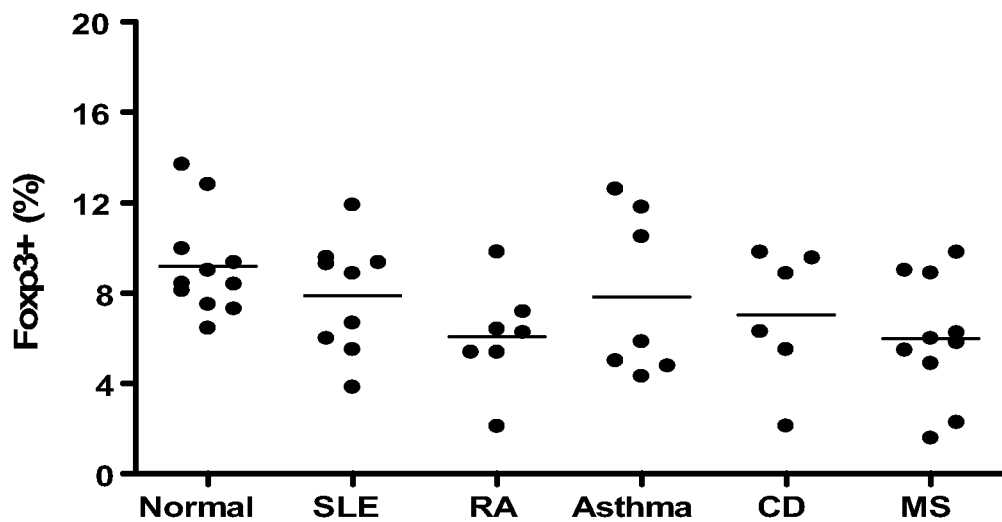
FIG. 1 is a graph showing the frequency of CD4+Foxp3+ Tregs from the population of Example 1.

The invention provides methods for the ex-vivo expansion of CD4+CD25+ Tregs, compositions resulting from the method and methods for use of the compositions. The cells resulting from use of the method demonstrate enhanced suppressive activities compared to fresh Treg cells. The invention provides a method for producing ex vivo expanded Tregs that may be used to inhibit unwanted human immune responses against self-antigens or allergens. Additionally, the ex vivo expanded Tregs may provide treatment for inflammatory/autoimmune diseases.

In one embodiment, the invention provides a methods comprising, consisting essentially of, and consisting of: a) obtaining a population of T cells from an individual; b) isolating and purifying from the T cell population a subpopulation of CD4+CD25+ Tregs; and c) expanding the Treg cells of the subpopulation, wherein the expanded Treg cells exhibit enhanced suppressive activity compared to a population of freshly purified, unexpanded Tregs from the individual.

It is a discovery of the invention that Tregs taken from a person with autoimmune/inflammatory diseases including, without limitation Systemic Lupus Erythematous ("SLE"), Multiple Sclerosis ("MS"), asthma, Rheumatoid Arthritis ("RA"), Crohn's Disease ("CD"), and Ulcerative Colitis ("UC), display enhanced suppressive activities to inhibit T cell proliferation when compared to freshly purified Tregs from the same person. It is a further discovery of the invention that the Tregs can be expanded 100 to 1,000 fold ex-vivo while having enhanced suppressive function.

In a first step of the method of the invention, a population of T cells is obtained. The T cells may be obtained from any suitable source including, without limitation, an individual's peripheral blood, thymus, lymph nodes, spleen or bone marrow. Preferably, the T cells are obtained from the peripheral blood of a person. More preferably, the T cells are obtained from an individual with an autoimmune/inflammatory diseases and most preferably from an individual with one or more of SLE, MS, asthma, RA, CD and UC whether the disease is in remission or during a period in which the disease is active. Most preferably, human CD4+CD25+ T regs are purified from whole blood units or leukpaks.

A subpopulation of CD4+CD25+ Tregs is then isolated from the T cell population using any convenient separation techniques based on Treg specific cell markers, including, without limitation, flow cytometry by any convenient method. For example, any number of kits for carrying out such isolation and purification are commercially available. The commercially available kits include, without limitation, Miltenyi Treg kit with Auotmacs, ClinMACS, and the like. Preferably, the isolation and purification is carried out until a population that is greater than 40% positive for Foxp3 and greater than 90% positive for CD4 is obtained.

The Treg subpopulation is then expanded ex-vivo using an autoantigen specific regulatory T cell stimulatory composition. Preferably, the composition antigen-specifically binds and activates the T cell receptor complex. More preferably, the expansion is carried out in the presence of effective amounts of a first and a second activator and a co-stimulator activator. By effective amount is meant an amount effective to stimulate the regulatory T cells to the degree desired.

The first activator is a TCR/CD3 activator that may be a multivalent antibody or ligand for TCR/CD3 including, without limitation, antigen non-specific activators such as an anti-CD antibody, and antigen-specific activators, such as an MHC-peptide multimer in which the peptide is an autoimmune/inflammatory disease associated peptide. Preferably, the TCR/CD3 activator is an anti-CD3 antibody.

The composition includes a second activator that is an additional suitable regulatory T cell stimulator. This component may include, without limitation an interleukin. Preferably IL-2 is used. The IL-2 typically is used in recombinant form and used in an amount of about 1,000 IU/ml.

A multivalent antibody or ligand specific for a TCR co-stimulator may be used as the co-stimulator activator. Preferably, the co-stimulator activator is CD28. The activator may be enhanced by use of one or more additives including, without limitation, rapamycin, a P13 kinase inhibitor, anti-IL6 and the like.

The TCR/CD3 activator and TCR co-stimulator activator preferably are immobilized on a three-dimensional solid surface, more preferably on a bead. Suitable beads are commercially available such as cell Expander Dynalbeads (Invitrogen). The Treg to bead ratio is preferably 1:3. Optimal bead size will depend on a consideration of the size required to efficiently congregate the antibodies and typically is about 1 to 10 microns in diameter. The anti-CD3 and anti-CD28 antibody ratio on the surface of the bead may vary from about 1 to 20 or about 20 to 1.

The expansion is carried out to at least a 100 fold expansion, preferably to a greater than 1,000. The expansion will depend upon the stimulation and length of the culture. However, other variations may be introduced into the culture the longer the length of the culture and, thus, a culture time that permits obtaining the most cells without a substantial introduction of other unfavorable factors is preferred.

The invention will be clarified by consideration of the following, non-limiting examples.

EXAMPLES

Example 1

Approximately 5 to 10 peripheral blood samples of 50 cc each were collected from 9 persons with SLE, 7 persons with RA, 7 persons with asthma, 10 persons with MS, and 7 persons with CD as well as from 11 persons with no autoimmune disease.

CD4+ Tregs were isolated and purified from the peripheral blood mononuclear cells ("PBMCs") of the samples. The PBMCs were isolated from blood samples by density gradient centrifugation with Ficoll Hypaque (Amersham). The CD4+CD25+Tregs were purified from PBMCs by autoMACS using the human CD4+CD25+ regulatory T cell isolation kit (Miltenyi Biotec, Auburn, CA) according to the manufacturer's instructions. Briefly, CD4+ T cells were first negatively isolated from PBMCs by depleting non CD4 cells with the mixture of monoclonal antibodies against human CD8, CD14, CD16, CD19, CD36, CD56, CD123, TCRy/8 and CD235a. Human CD4+CD25+ Tregs were then positively isolated with anti-human CD25 antibody-conjugated microbeads from the enriched CD4+ T cell population. The frequency of Foxp3-expressing CD4+ Tregs was assessed using intracellular Foxp3 staining and analyzed by flow cytometry. The results are displayed in FIG. 1 below in which the percentage of CD4+Foxp3+Tregs in the CD4+ pool population from each person is shown.

Example 2

Approximately 5 to 10 peripheral blood samples of 50 cc each were collected from 9 persons with SLE, 7 persons with RA, 7 persons with asthma, 8 persons with MS, and 7 persons with CD as well as from 25 persons with no autoimmune disease.

Figure 2:
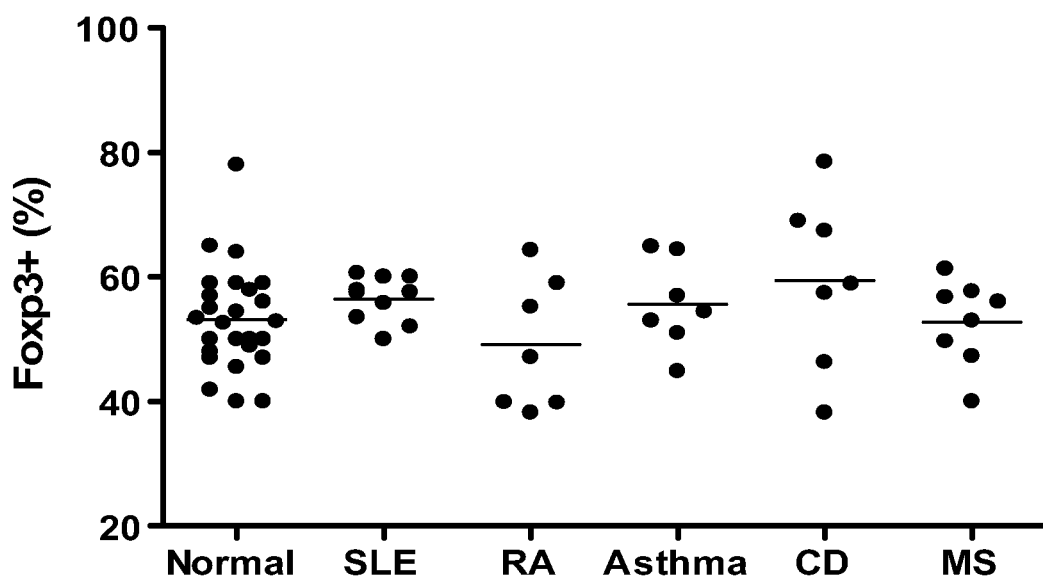
FIG. 2 is a graph showing the purity CD4+ Tregs of Example 2.

CD4+ Tregs were purified from the PBMCs of the samples. Purification was carried out using as set forth in Example 1. The purity of purified CD4+ Tregs at day 0 was assessed using intracellular Foxp3 staining and analyzed by flow cytometry and the results are displayed on the graph in FIG. 2. Approximately 40 to 75% of the purified cells expressed Foxp3.

Example 3

Approximately 5 to 10 peripheral blood samples of 50 cc each were collected from persons with SLE (FIG. 3A), RA (FIG. 3C), asthma (FIG. 3B), MS (FIG. 3D), CD (FIG. 3E), and UC (FIG. 3F). CD4+ Tregs were purified from the PBMCs of the samples. Purification was carried out using as set forth in Example 1.

Figure 4:
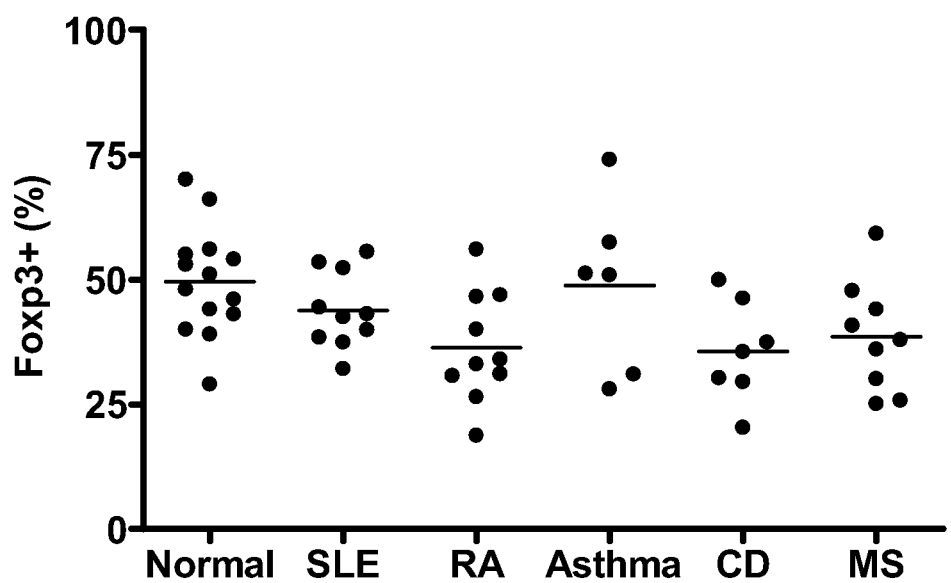
FIG. 4 is a graph showing the percentage of ex-vivo expanded cells of Example 3 that expressed Foxp3.

The CD4+Foxp3+ Tregs were cultured in X-VIVO 15™ media (Cambrex Bio-Whitaker, East Rutherford, NJ) supplemented with 10% pooled human AB serum (Cambrex) in the presence of 1000 IU/MI of human rIL-2 (Proleukin). In addition, anti-CD3/ant-CD28 coated beads (Dynal, Oslo, Norway) were added at a 1:3 cell to bead ratio. After 3 weeks of culture at 37° C. in an incubator, the expanded Tregs reached over 100 to 1,000 fold expansion, or 1 billion cells, as shown in the graphs in FIG. 3. In FIG. 4 is a graph depicting that an average of 40 to 50% of the ex-vivo expanded cells expressed Foxp3 by intracellular staining at 2 weeks.

Example 4

The Tregs of Example 3 were evaluated at week 2 with standardized suppressive assays as follows. For anti-CD3 stimulated cultures, allogenic CD4+CD25+ human T cells ($5 \times 10^4$ cells/well) from the same donor were used as responder cells, 1 mg/ml anti-CD3 (OKT3), and allogenic human dendritic cells (from one donor, $5 \times 10^3$ cells/well) and serially diluted expanded Tregs were put in 96-well plates in triplicate. For alloantigen stimulated cultures, CD4+CD25+ human Treg cells ($5 \times 10^4$ cells/well) from one donor, $5 \times 10^3$ human dendritic cells from another donor, and serially diluted expanded Tregs were plated in triplicate in 96-well plates.

The results, shown in the graphs of FIGS. 5A and 5B (SLE), FIGS. 5C and 5D (asthma), FIGS. 5E and 5F (RA), FIGS. 5G and 5H (MS), FIGS. 5I and 5J (CD), and FIGS. 5K and 5L (UC), demonstrate that the ex vivo expanded human Tregs had potent inhibitory activity to inhibit T cell proliferation in in vitro functional assays. Additionally, the Tregs' inhibitory activity was enhanced as compared to that of freshly purified Tregs from the same persons. This suppressive activity may be used to inhibit unwanted human immune responses in autoimmune/inflammatory diseases and provide a clinical therapeutic potential for autoimmune/inflammatory diseases.

What is claimed is:

1. A method of preparing a population of cells, the method comprising:
   a) obtaining a population of T cells from an individual with an immune-mediated disease selected from Systemic Lupus Erythematous, Multiple Sclerosis, asthma, Rheumatoid Arthritis, Crohn's Disease, or Ulcerative Colitis;
   b) isolating and purifying from the T cell population a subpopulation of CD4+CD25+ Tregs; and
   c) expanding the Treg cells of the subpopulation over 1,000 fold, in the presence of IL-2, anti-CD3 antibodies, and anti-CD28 antibodies, wherein the expanded Treg cells exhibit enhanced suppressive activity compared to a population of freshly purified, unexpanded Tregs from the individual;
   wherein the anti-CD3 antibodies and anti-CD28 antibodies are immobilized on a three-dimensional solid surface.

2. The method of claim 1, wherein the immune-mediated disease is Systemic Lupus Erythematous.

3. The method of claim 1, wherein the immune-mediated disease is Multiple Sclerosis.

4. The method of claim 1, wherein the immune-mediated disease is asthma.

5. The method of claim 1, wherein the immune-mediated disease is Rheumatoid Arthritis.

6. The method of claim 1, wherein the immune-mediated disease is Crohn's Disease.

7. The method of claim 1, wherein the immune-mediated disease is Ulcerative Colitis.

8. The method of claim 1, wherein the expansion is carried out over a period of about 3 weeks.

9. The method of claim 1, wherein the three-dimensional solid surface is a bead.

10. The method of claim 9, wherein a Treg to bead ratio is 1:3.

11. The method of claim 9, the bead is about 1 to 10 microns in diameter.

12. The method of claim 9, wherein an anti-CD3 and anti-CD28 antibody ratio on the surface of the bead is from about 1:20 to about 20:1.

* * * * *